US00PP34372P2

(12) United States Plant Patent
Noack

(10) Patent No.: US PP34,372 P2
(45) Date of Patent: Jun. 28, 2022

(54) SHRUB ROSE PLANT NAMED 'NOA813219'

(50) Latin Name: *Rosa hybrida*
Varietal Denomination: NOA813219

(71) Applicant: Reinhard Noack, Gutersloh (DE)

(72) Inventor: Reinhard Noack, Gutersloh (DE)

( * ) Notice: Subject to any disclaimer, the term of this patent is extended or adjusted under 35 U.S.C. 154(b) by 0 days.

(21) Appl. No.: 17/345,804

(22) Filed: Jun. 11, 2021

(51) Int. Cl.
*A01H 5/02* (2018.01)
*A01H 6/74* (2018.01)

(52) U.S. Cl.
USPC ..... Plt./106

(58) Field of Classification Search
USPC ..... Plt./101, 102, 105, 106
See application file for complete search history.

(56) References Cited

PUBLICATIONS

Backhaus-Cysyk. 2019. New roses for 2019: 'Saloon', 'Jojo Peach' and 'Balou'. https://taspo.de/kategorien/neue-rosen-fuer-2019-saloon-jojo-peach-und-balou/. 3 pages.*
Noack Rosen. 2021. https://noack-rosen.de/sortenschutz-markenschutz/. 18 pages.*

* cited by examiner

*Primary Examiner* — Karen M Redden
(74) *Attorney, Agent, or Firm* — Cassandra Bright

(57) ABSTRACT

A new and distinct cultivar of *Rosa* plant for garden use named 'NOA813219' is disclosed, characterized by single orange/pink flowers on plants with rapid re-flowering. Plants have excellent resistance to blackspot, powdery mildew, downy mildew and rust diseases. Plants are dense and compact with uniform growth and are well suited for landscape use, especially as a groundcover. The new variety is a *Rosa*, normally produced as an outdoor garden or container plant.

2 Drawing Sheets

Figure 1:
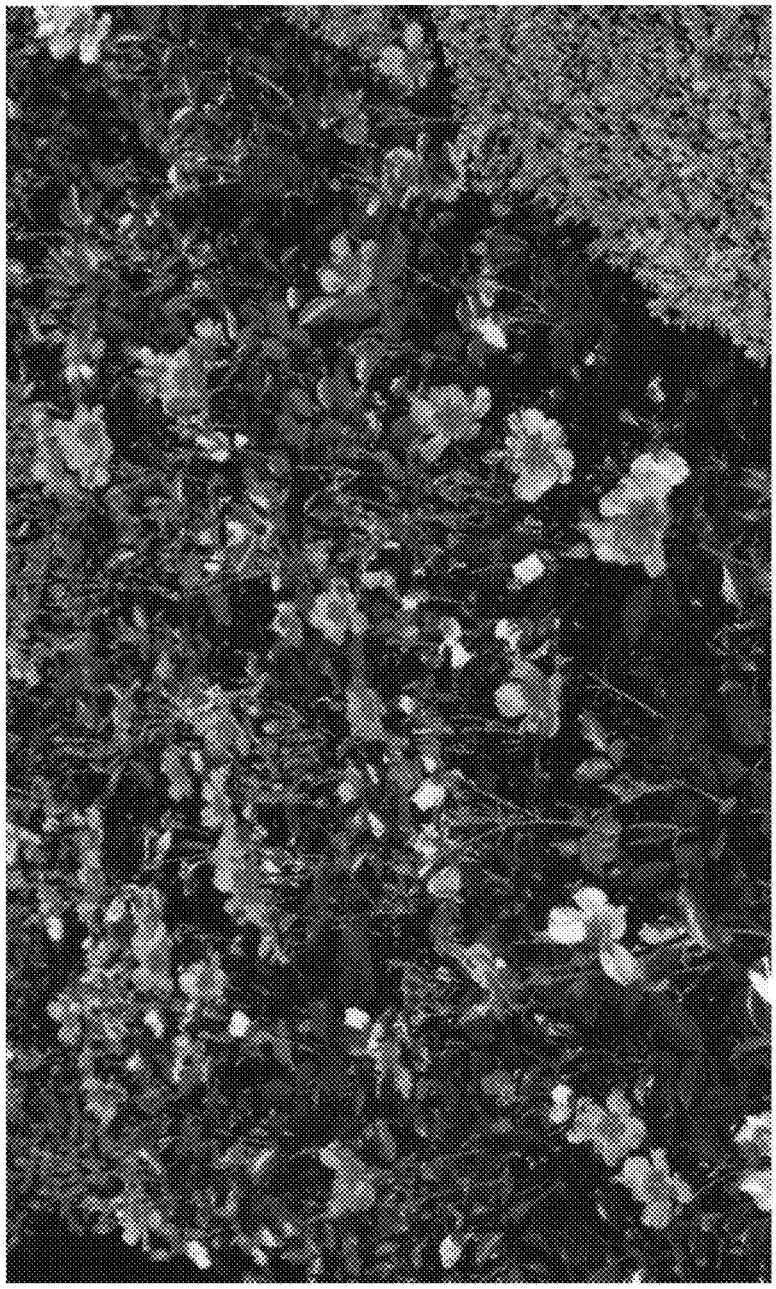

Latin name of the genus and species: *Rosa hybrida.*
Variety denomination: 'NOA813219'.

BACKGROUND OF THE INVENTION

The new *Rosa* cultivar is a product of a planned breeding program conducted by the inventor, Reinhard Noack, conducted in Gutersloh, Germany. The objective of the breeding program was to create a new and distinct landscape rose plants with unique qualities such as, uniform growth and excellent resistance to diseases encountered in landscapes and gardens. These objectives have been substantially achieved and in that distinguish 'NOA813219' from all other varieties of which the inventor is aware. This combination of qualities is not present in prior rose cultivars known to the inventor. The cross resulting in this new variety was made during May of 2012.

The seed parent is an unnamed, unpatented, proprietary *Rosa hybrida*. The pollen parent is a different unpatented, unnamed proprietary *Rosa hybrida*. The new variety was discovered in April of 2013 by the inventor in a group of seedlings resulting from the 2012 crossing, in a research greenhouse in Gutersloh, Germany.

Asexual reproduction of the new cultivar was performed by terminal semi-soft wood vegetative cuttings. This was first performed at a research greenhouse in Gutersloh, Germany in Summer of 2013 and has shown that the unique features of this cultivar are stable and reproduced true to type in successive generations.

SUMMARY OF THE INVENTION

The cultivar 'NOA813219' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NOA813219' These characteristics in combination distinguish 'NOA813219' as a new and distinct *Rosa* cultivar:

1. Orange/pink single flowers.
2. Dense, compact habit.
3. Plants have excellent resistance to blackspot, powdery mildew, downy mildew and rust diseases.
4. Plants reflower quickly
5. Suitability for groundover purposes.
6. Unique conspicuous orange stamens.
7. Uniform growth.
8. Easy to grow.

Plants of the new cultivar 'NOA813219' are similar to plants of the seed parent, in most horticultural characteristics, however, plants of the new cultivar 'NOA813219' differ in the following:

1. The new variety has orange/pink flowers; the seed parent has orange flowers.
2. The new variety has a single flower; the seed parent has a double flower.
3. The new variety grows to approximately 50 cm; the seed parent grows to approximately 90 cm.

Plants of the new cultivar 'NOA813219' are similar to plants of the pollen parent in most horticultural characteristics, however, plants of the new cultivar 'NOA813219' differ in the following;

1. The new variety has orange/pink flowers; the pollen parent has pink flowers.

2. Plants of the new variety have very good resistance to diseases typical of garden roses; plants of the pollen parent have average resistance to the same diseases.
3. Flowers of the new variety are weakly fragrant; flowers of the pollen parent are strongly fragrant.

COMMERCIAL COMPARISON

Plants of the new cultivar 'NOA813219' can be compared to the commercial variety *Rosa* 'Noare', U.S. Plant Pat. No. 11,308. These varieties are similar in most horticultural characteristics, however 'NOA813219' differs in the following:

1. The new variety has orange/pink flowers; this comparator has red flowers.
2. Plants of 'NOA813219' are more upright than plants of 'Noare'

Plants of the new cultivar 'NOA813219' can also be compared to the commercial variety *Rosa* 'Flower Carpet White' U.S. Plant Pat. No. 9,573. These varieties are similar in most horticultural characteristics; however, 'NOA813219' differs in the following:

1. The new variety has orange/pink flowers; this comparator has red flowers.
2. Flowers of 'NOA813219' are smaller in diameter than flowers of this comparator.

BRIEF DESCRIPTION OF THE PHOTOGRAPHS

The accompanying photograph in FIG. 1 illustrates in full color a planting of 'NOA813219'. Age of the plants photographed is approximately 3 years.

Figure 2:
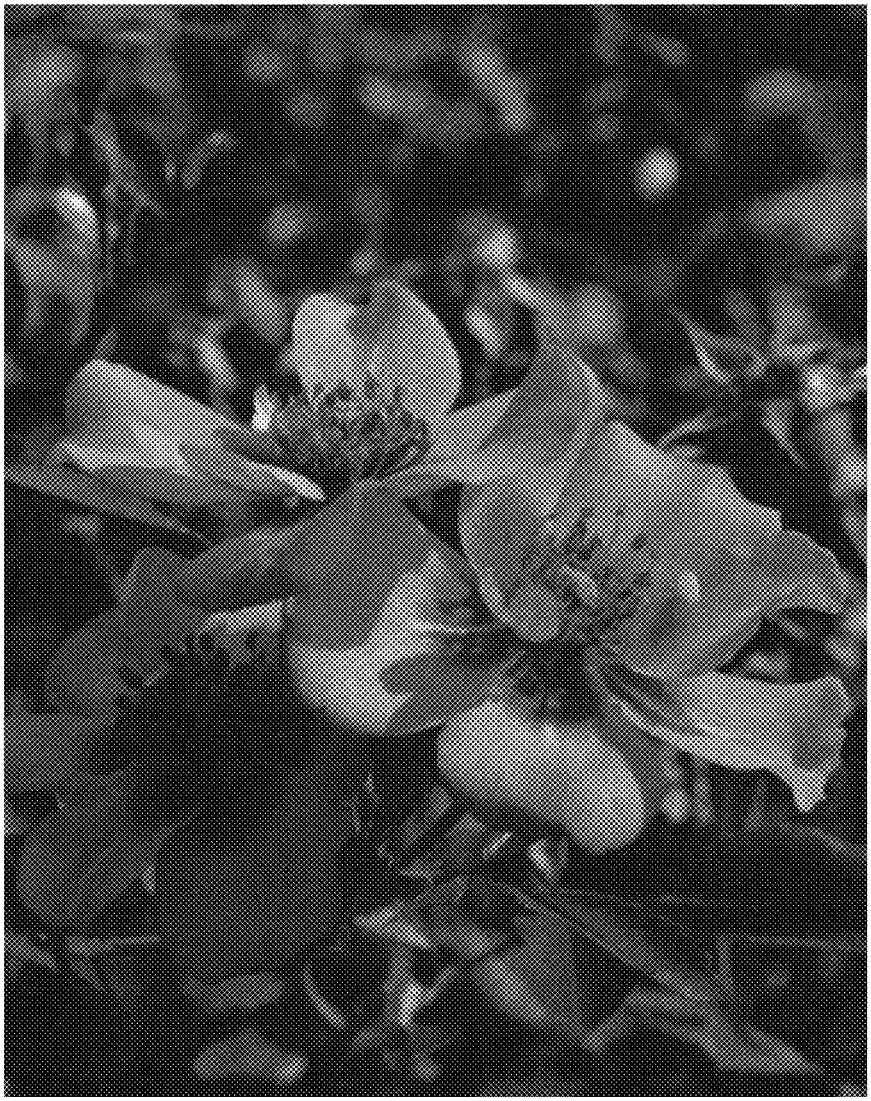

FIG. 2 illustrates a close-up view of typical flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'NOA813219' plants grown outdoors, in Gutersloh, Germany. The growing temperature ranged from approximately −1° C. to 35° C. during the day and from approximately −16° C. to 20° C. during the night. General light conditions are bright, normal sunlight. Measurements and numerical values represent averages of typical plant types.

Botanical classification: *Rosa* 'NOA813219'.

Commercial classification: Groundcover rose.

PROPAGATION

Time to initiate roots: About 42 days at approximately 20° C.

Time to produce a rooted cutting: About 90 days at approximately 15° C.

PLANT

Age of plant described: Approximately 3 years, planted in the ground.

Growth habit: Upright.

Mature height: 50 cm.

Mature plant spread: 40 cm.

Rootstock: Own root.

Growth rate: Approximately 80 to 90 cm per year.

Branching characteristics: Sympodial branching.

Length of primary lateral branches: Average 30 cm.

Diameter of lateral branches: Approximately 4 mm.

Quantity of lateral branches: Approximately 8-12.

Branching arrangement: Alternate.

Branches-young wood:

- *Diameter.*—Approximately 3 to 4 mm.
- *Texture.*—Glabrous.
- *Approximately density/quantity of thorns.*—Dense prickles.
- *Color.*—Near Green 143D, weakly flushed with anthocyanin Greyed-Purple 187A.

Branches-old wood:

- *Diameter.*—Approximately 1.5 cm, after 3 years.
- *Color.*—Near Green RHS 137C, with brown tinge not accurately described with R.H.S. chart.
- *Texture.*—Smooth.
- *Approximately density/quantity of thorns.*—Dense, fine prickle-like thorns.

FOLIAGE

Leaf:

- *Arrangement.*—Alternate.
- *Quantity.*—Approximately 25 per main branch.
- *Average length.*—Approximately 9 cm.
- *Average width.*—Approximately 6 cm.

Leaflet:

- *Quantity.*—Approximately 5 to 7 per leaf.
- *Average length.*—Approximately 5 cm.
- *Average width.*—Approximately 2.0 cm.
- *Shape of blade.*—Ovate.
- *Apex.*—Acuminate.
- *Base.*—Obtuse.
- *Margin.*—Serrated.
- *Appearance of top surface.*—Weak to moderately glossy.
- *Appearance of bottom surface.*—Matte.
- *Texture of top surface.*—Non-pubescent.
- *Texture of bottom surface.*—Non-pubescent.
- *Leaf internode length.*—Average 3 to 5 cm.
- *Color.*—Young foliage upper side: Near Yellow-Green RHS 147A. Anthocyanin near Greyed-Purple 183C, strongest along margin. Young foliage under side: Near Yellow-Green RHS 147B. Mature foliage upper side: Near Yellow-Green RHS 147B. Mature foliage under side: Near Yellow-Green RHS 147C.
- *Venation.*—Type: Pinnate. Venation color upper side: Near Yellow-Green N144A. Venation color under side: Near Yellow-Green 150A.

Petiole:

- *Average length.*—Approximately 3 cm.
- *Average diameter.*—Approximately 5 mm.
- *Color.*—Near RHS Yellow-Green N144A.
- *Texture.*—Glabrous, matte.

Rachis:

- *Average length.*—Average range 7.0 to 9.0 cm.
- *Average diameter.*—Approximately 5 mm.
- *Texture.*—Glabrous.
- *Color.*—Near RHS Greyed-Red 178A Stipule:
*Average length*.—Average range 2.0 to 2.5 cm.
*Average diameter*.—Approximately 1.0 cm.
*Texture*.—Glabrous.
*Color*.—Near RHS Yellow-Green N144D, very lightly flushed with Greyed-Red 178C.

FLOWER

Natural flowering season: Spring until mid-Fall.
Begins flowering after how many years/months: As early as 3 months from a rooted liner.
Inflorescence type and habit: Single whorled flowers occurring 3 to 5 per flowering node. Flowers weakly upwardly cupped.
Rate of flower opening: Approximately 5 days from bud to fully opened flower.
Individual flower size:
*Diameter*.—Approximately 4 cm.
*Depth*.—Approximately 3 cm.
Pedicel:
*Length*.—5 to 6 cm.
*Diameter*.—4 mm.
*Texture*.—Glabrous.
*Color*.—Near RHS Yellow-Green N144B.
Petals:
*Petal arrangement*.—Rotate, overlapping.
*Size*.—Length: Average 2 cm. Width: Average 1.7 to 2 cm.
*Shape*.—Obovate.
*Margin*.—Entire, non-ruffled.
*Apex*.—Obtuse, rounded.
*Base*.—Obtuse.
*Petal quantity*.—Average range 8 to 15.
*Texture*.—Smooth.
Color:
*Petals*.—When opening: Upper surface: Near RHS Red 41A and Red 39B, base near Yellow-Orange 22C. Lower surface: Near RHS Red 41A and Red 39B, base near Yellow-Orange 22C. Fully opened: Upper surface: Near RHS Red 41D and Red 39B, base streaked near Yellow-Orange 22C. Lower surface: Near RHS Red 41D and Red 39B, base streaked near Yellow-Orange 22C.
Bud:
*Shape*.—Ovate.
*Length*.—Approximately 2 cm.
*Diameter*.—Approximately 1 cm.
*Color*.—Near Yellow-Green 146B.
Sepals:
*Length*.—1.5 cm.
*Width*.—1.0 cm.
*Shape*.—Lanceolate.
*Color*.—Interior Surface: Near RHS Yellow-Green N144C. Exterior Surface: Near RHS Yellow-Green N144D.
*Texture*.—Densely puberulent interior and exterior surfaces.
*Sepal extensions*.—Weak.
*Quantity*.—Average 5 per flower.
*Receptacle*.—Length: 1.0 cm. Width: 1.5 to 2.0 cm. Shape: Pitcher shaped. Color: Near RHS Yellow-Green N144D.
*Fragrance*.—Weak.

REPRODUCTIVE ORGANS

Stamens:
*Number*.—Approximately 40-60.
*Filament length*.—Approximately 3 mm.
*Filament color*.—Near RHS Orange-Red 33B.
Anthers:
*Length*.—1 mm.
*Shape*.—Narrow ovate.
*Color*.—Near Orange 26A.
*Pollen*.—Color: Near Yellow-White 158D. Quantity: Moderate.
Pistil:
*Number*.—Approximately 10-15.
*Pistil length*.—Approximately 4 mm.
*Style*.—Length: Approximately 2 mm. Color: Light green to cream, not accurately determined with R.H.S. chart.
*Stigma*.—Shape: Linear. Color: Light green to cream, not accurately determined with R.H.S. chart.

OTHER CHARACTERISTICS

Seeds and fruits: Not observed to date. Fruits typically dry up, without fully forming.
Disease/pest resistance: Excellent resistance to blackspot, powdery mildew, downey mildew and rust. Average resistance to normal pests of garden roses.

What is claimed is:

1. A new and distinct groundcover rose plant named 'NOA813219' as herein illustrated and described.

* * * * *